United States Patent [19]
Willis et al.

[11] Patent Number: 5,799,058
[45] Date of Patent: Aug. 25, 1998

[54] X-RAY MACHINE CONE LOCATOR ATTACHED TO RADIOGRAPHIC FILM HOLDER

[76] Inventors: Timothy G. Willis, 310 Evergreen, Yreka, Calif. 96097; Timothy J. Landis, 8559 Washington Blvd., Roseville, Calif. 95678

[21] Appl. No.: 823,496

[22] Filed: Mar. 25, 1997

Related U.S. Application Data

[63] Continuation of Ser. No. 563,992, Nov. 29, 1995, Pat. No. 5,625,666.
[51] Int. Cl.⁶ ........................................... A61B 6/14
[52] U.S. Cl. .......................................... 378/168
[58] Field of Search ........................... 378/168, 167, 378/170, 177

[56] References Cited

U.S. PATENT DOCUMENTS

| | | |
|---|---|---|
| 4,554,676 | 11/1985 | Maldonado et al. ............ 378/170 |
| 5,289,522 | 2/1994 | Kanbar et al. .................. 378/170 |
| 5,327,477 | 7/1994 | Levy ................................ 378/168 |

*Primary Examiner*—Don Wong
*Attorney, Agent, or Firm*—Julian Caplan; Flehr Hohbach Test Albritton & Herbert LLP

[57] ABSTRACT

A ring is shaped to fit over the nose of a dental x-ray machine to direct the x-rays to the desired portions of the patient's mouth. Known film retainers which support x-ray film packets at the desired location behind the gums have handles which extend outside the mouth. The ring has adjustable means to fit onto the handle to adjust the position of the ring relative to the film both angularly and distance-wise. An adapter may be used to connect the ring to the handle of the retainer. Alternatively, the handle may slide through an aperture in a tab fixed to the ring.

12 Claims, 5 Drawing Sheets

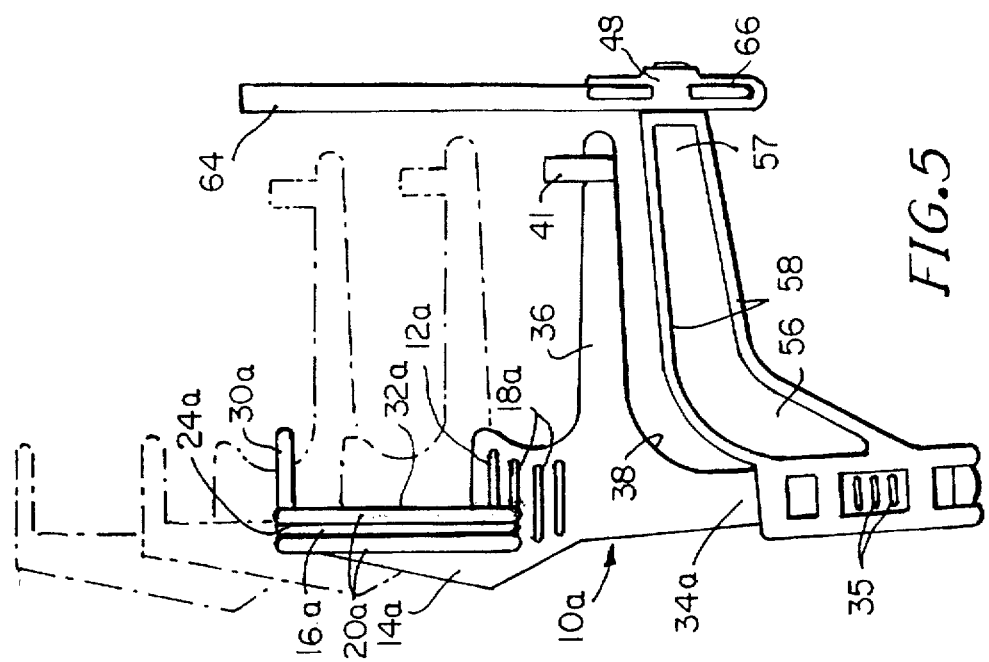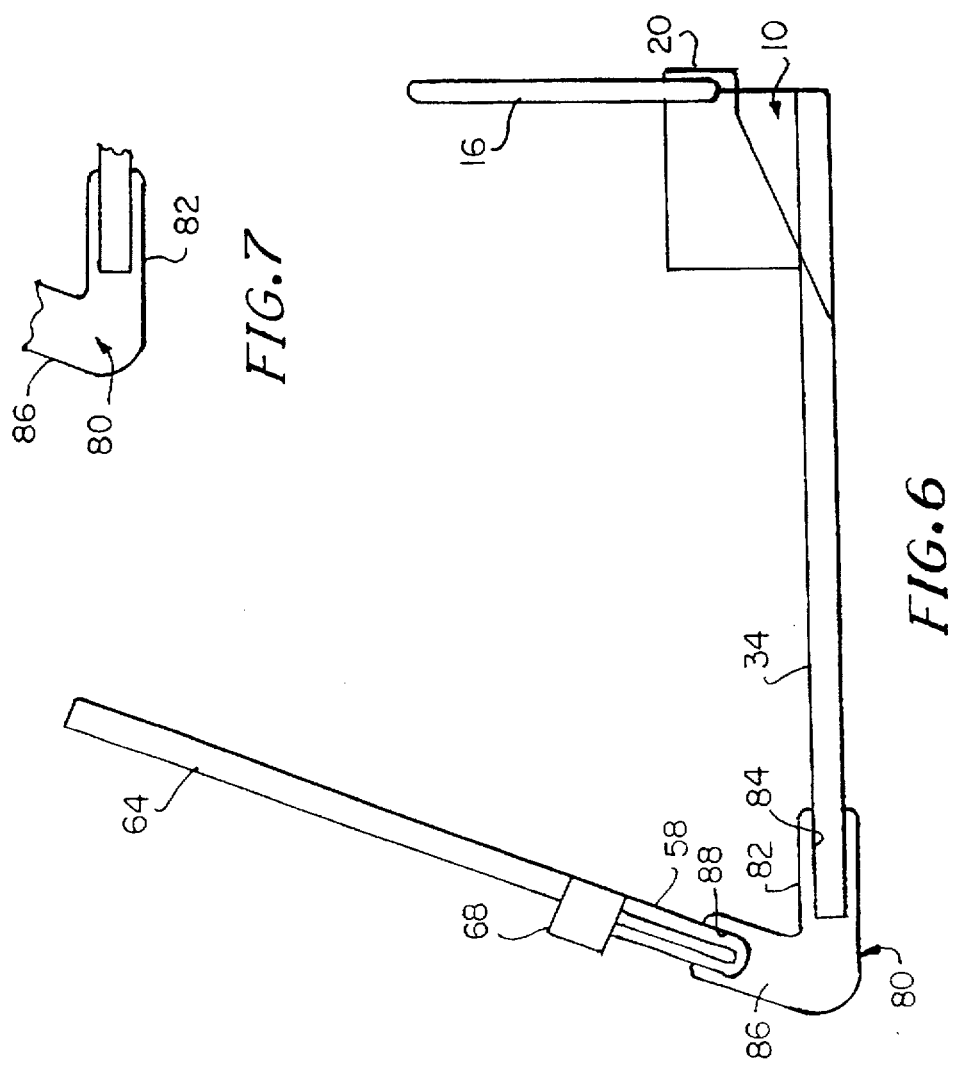

X-RAY MACHINE CONE LOCATOR ATTACHED TO RADIOGRAPHIC FILM HOLDER

CROSS REFERENCE TO RELATED APPLICATIONS

This invention is a continuation-in-part of Willis U.S. application Ser. No. 08/563,992 filed Nov. 29,1995 on Radiographic Film Retaining Device, now U.S. Pat. No. 5,625,666 issued Apr. 29,1997 which was an improvement upon Willis U.S. Pat. No. 5,256,982 issued Oct. 26, 1993.

BACKGROUND OF THE INVENTION

1. Field of the invention.

This invention relates in general to the combination of a radiographic film holder useful in dentistry and an x-ray machine cone locator. The combination locates a film packet relative to the teeth to be filmed and the cone or nose of the x-ray machine so as to facilitate filming selected portions of the upper teeth, lower teeth or the teeth of both jaws simultaneously.

2. Prior Art

The prior art known to applicants is set forth in detail in the specifications of said application Ser. No. 08/563992 and in said U.S. Pat. No. 5,256,982. A feature of the present invention is the provision of a detachable locator having a ring dimensioned to receive the cone of a dental x-ray machine and means associated with the ring for connection to the handle of a film holder.

SUMMARY OF THE INVENTION

The invention comprises essentially two detachable but interfitting members. One member maybe any of a plurality of different radiographic film-retaining devices suitable for holding a film packet used to produce a radiographic image of selected teeth of a patient's mouth. Such retaining device includes a thin bite portion which is configured for placement between the upper and lower teeth of the mouth. Distally of the bite portion, is a grip for a film packet. When the patient bites down on the bite portion, gripping it between his jaws, the retaining structure holds the film packet lingually adjacent to selected teeth. Such a retainer is formed with a handle which extends out through the lips and is used by the technician for adjustment purposes.

In accordance with the present invention, a locator is formed with a ring shaped to fit around the exterior of a dental x-ray machine nose or cone to direct the x-rays emitted therefrom toward the film held in the holder. The ring is provided with an extension which fits over a portion of the handle, whereby positioning of the film and the cone of the x-ray machine are coordinated. The connection between the holder and the handle of the retainer is such that the angle of the cone relative to the packet of film may be adjusted and, further, the distance between the cone and the packet maybe adjusted, all while maintaining proper alignment of the emitted x-rays in the plane of the film.

A further feature of the invention is the fact that the locator maybe used with either the retainer shown in U.S. Pat. No. 5,256,982, or that shown in Ser. No. 08/563992.

BRIEF DESCRIPTION OF THE DRAWINGS

FIG. 5 is a schematic view showing the structure of FIG. 4 in several different positions of adjustment.

FIG. 6 is a schematic view showing the locator and retainer interconnected by an adapter.

FIG. 7 is an enlarged side elevational view of the adapter.

DETAILED DESCRIPTION OF THE PREFERRED EMBODIMENTS

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Figure 3:
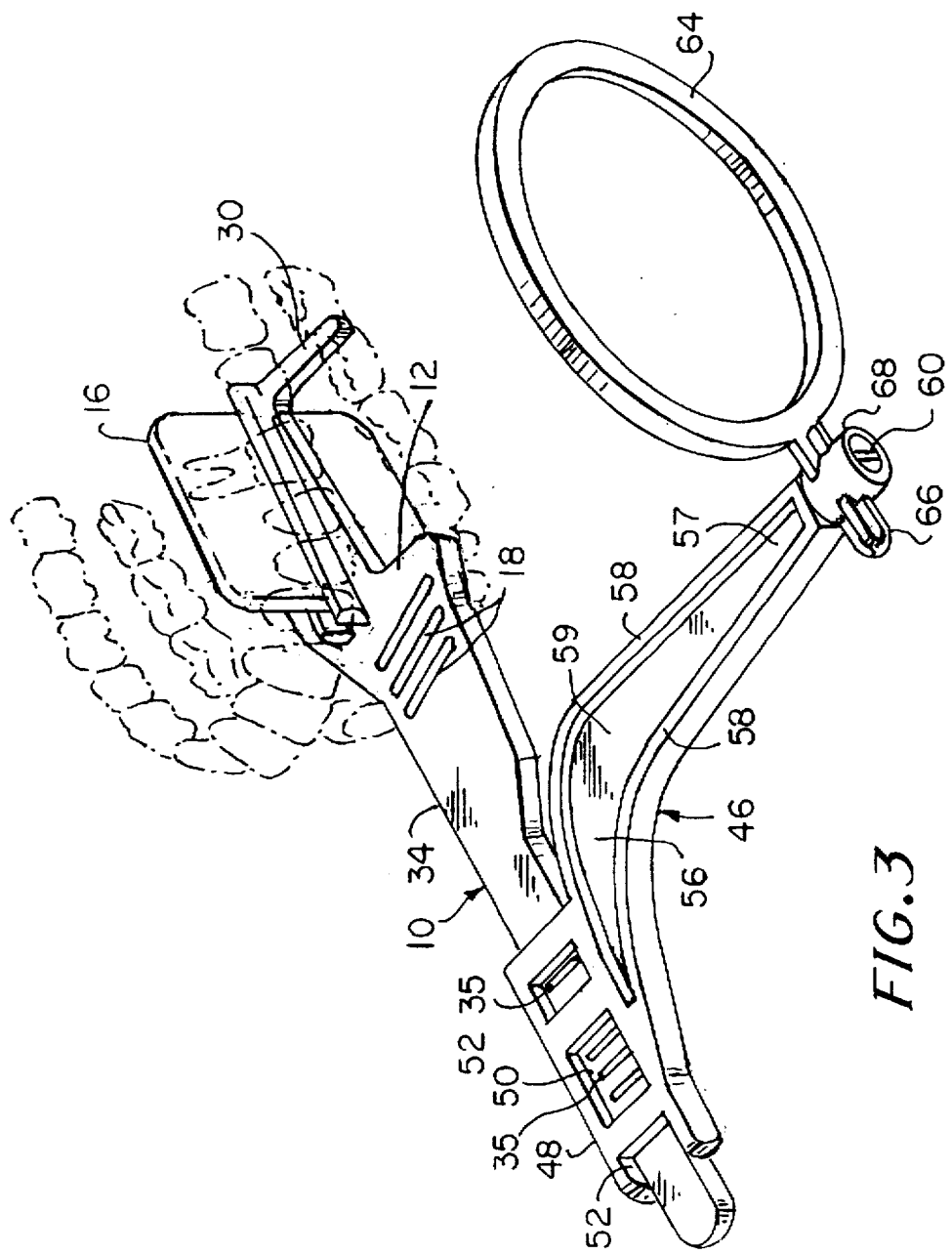
FIG.3 is a perspective view showing the structure of FIGS. 1 and 2 connected to a film retainer held between the upper and lower teeth of the patient.

Retainer 10 shown in FIG. 3 is similar to that shown in U.S. Pat. No. 5,256,982. It comprises a bite portion 12 which fits in the patient's mouth and has a distal film retaining structure 14 to receive a film packet 16. Ridges 18 formed on bite portion 12 hold the retainer in position when the patient bites thereon. Gripping members 20 on the distal end 22 provide a slit 24 therebetween into which the film packet 16 may be inserted in various positions, depending upon the particular teeth to be x-rayed. Extending outwardly is handle 34, which protrudes out the patient's lips and has transverse ridges 35 formed thereon.

Locator 46 receives handle 34. Accordingly, locator 46 is formed with a socket 48, which slidably receives the outer end of handle 34 and is provided with an integral detent 50, which engages the ridges 35 to secure the parts in desired position of adjustment. It will be understood the handle 34 maybe moved longitudinally of socket 48 for such adjustment. Extending outwardly relative to socket 48 is an arm 54, having a curved portion 56 adjacent socket 48 and a distal portion 57 at right angles to handle 34. The edges of portions 56 and 57 are formed with reinforcements 58, to rigidify the structure. At the outer end of distal end 57, is a split boss 60. The distal end 57 is formed with radial ridges 62, for a purpose which hereinafter appears.

Figure 1:
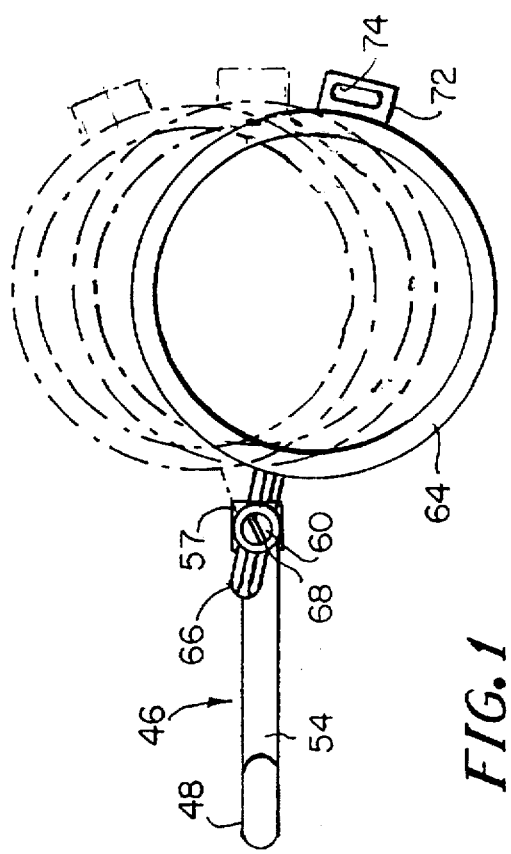
FIG. 1 is an elevational view of a locator in accordance with the present invention shown in three different positions of adjustment.
Figure 2:
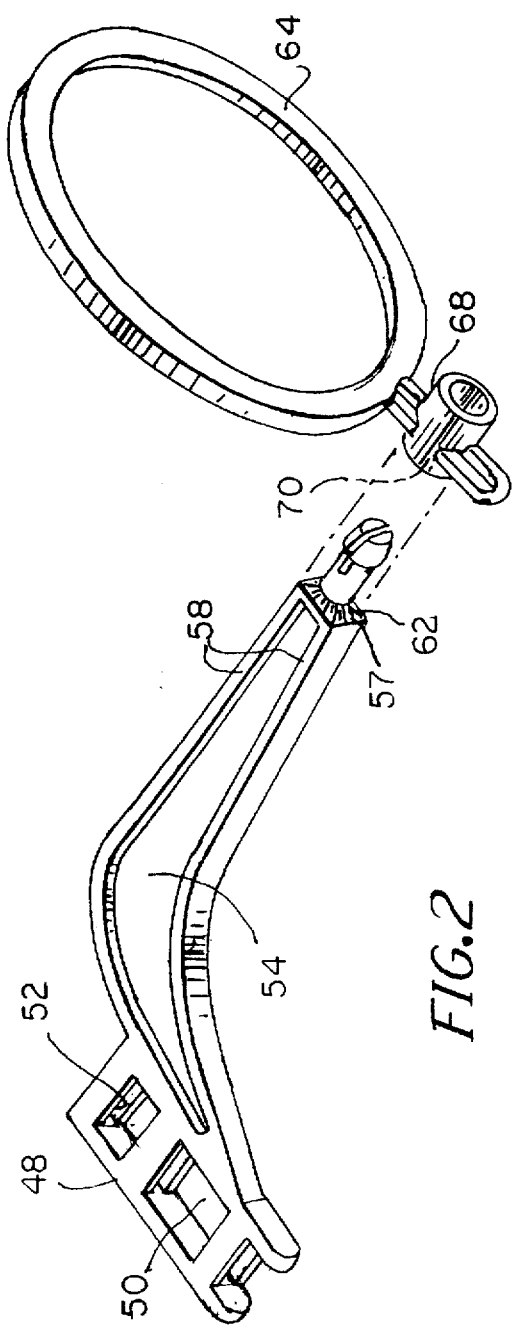
FIG. 2 is an exploded perspective view of the structure of FIG. 1 with one of the elements removed.

Ring 64 is dimensioned to receive the end of an x-ray machine tip or cone. Extending outwardly of ring 64 is arm 66 formed approximately midway of its length with a sleeve 68, which fits over boss 60. Ridges 70 are formed in one end of sleeve 68 to engage the ridges 62 on end 57, so as to hold the ring 68 in different positions of pivotal adjustment relative to curved portion 56. Referring to FIG. 1 it will be seen that the ring 64 maybe located in at least three different positions. The upper and lower positions maybe used to x-ray upper teeth or bottom teeth including the roots thereof; whereas the intermediate position maybe used to x-ray both the top and bottom teeth at one time.

Optionally, opposite arm 66 is an outwardly projecting tab 72 formed with a rectangular opening 74. If desired, the handle 34 of the retainer 10 shown in FIG. 3, maybe inserted though the opening 74. The distance by which the handle 39 is inserted, controls the distance between the film pack 16 and ring 64.

Figure 8:
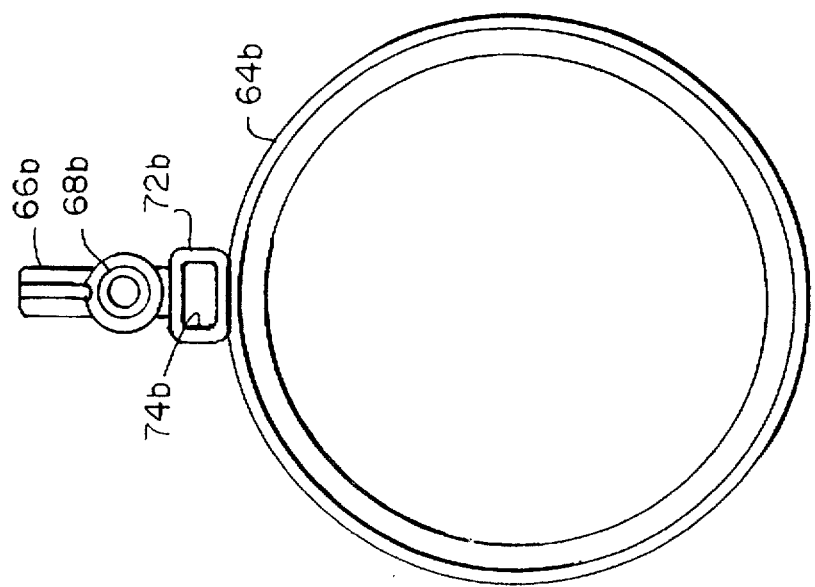
FIG. 8 is a plan view of a modified locator.

As shown in FIG. 8, tab 72b, formed with opening 74b, may optionally be located between ring 64b and sleeve 68b.

Figure 4:
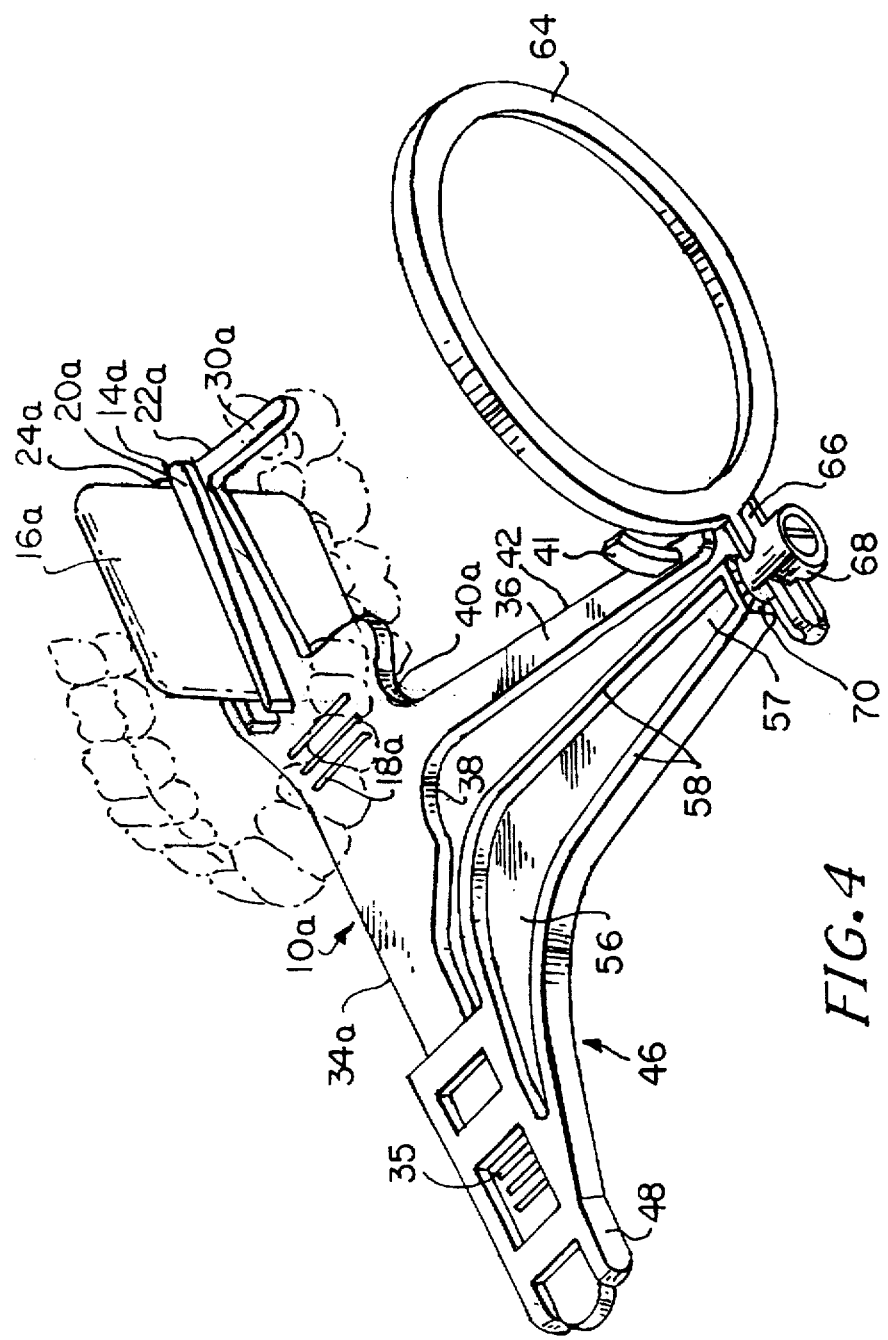
FIG. 4 is a view similar to FIG. 3 showing use of a modified retainer.

In a modified retainer, 10a shown in FIGS. 4 and 5, the structure shown in application Ser. No. 08/563992 is employed. Many of the parts of the structure of retainer 10a resemble those of the preceding modification and the same reference numerals followed by subscript a are used to designate corresponding parts. As explained in said application Ser. No. 08/563992, arm 36 extends outwardly, approximately perpendicular to slit 24a, there being a curved edge 38 connecting arm 36 to handle 34a. An arcuate locator 41 is disposed on the outer end of arm 36 and this is an alternative means to locate the cone of the x-ray machine. In other words, ring 64 may be a substitute for the arcuate locator 41. Inner edge 42 of arm 36 cooperates with locator 41 in this usage.

A further modification of the invention is shown in FIGS. 6 and 7. Adaptor 80 is formed with branches 82 and 86 disposed at an angle of approximately 70° with respect to each other. Branch 82 is formed with a groove shaped to receive the end of handle 34 and branch 86 is formed with a groove 88 to receive socket 48. As is best seen in FIG. 6, the center of ring 64 is located to direct the x-rays at the packet 16 for what is termed bi-angle x-ray.

Figure 9:
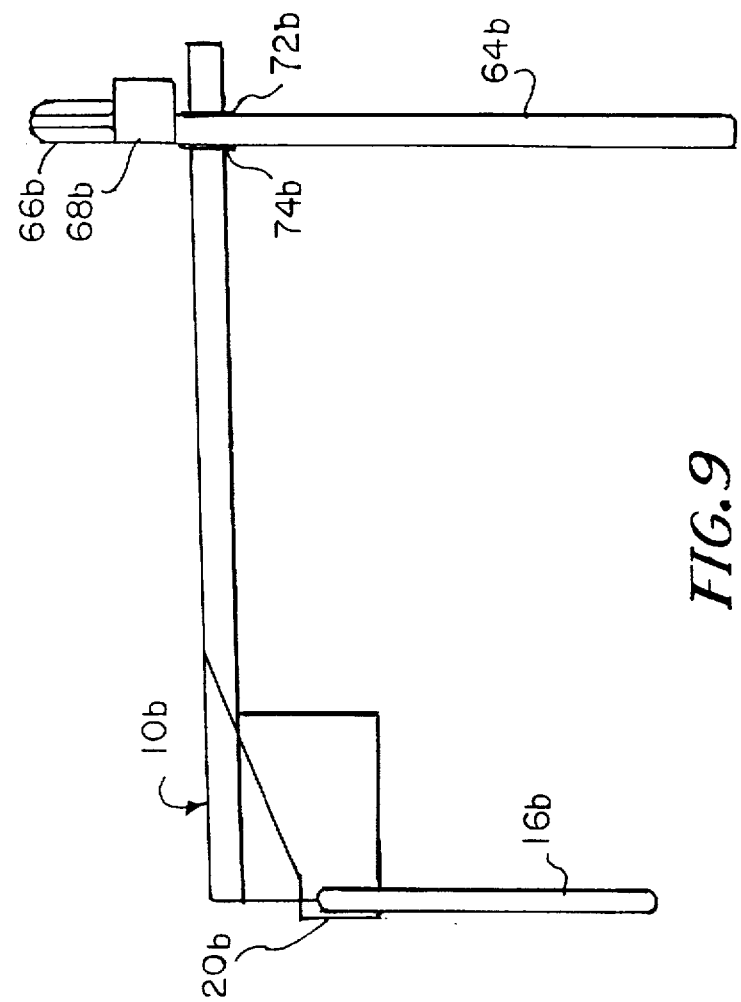
FIG. 9 is a view similar to FIG. 6 showing the locator of FIG. 8 and retainer interconnected.

FIG. 9 shows the locator of FIG. 8 in use. Handle 34b is inserted through opening 74b. The distance between film packet 16b and ring 64b may be adjusted by moving handle 34b in and out of the opening 74b in tab 72b (and hence the x-ray cone received in ring 64b). It will be seen that the x-rays are directed in-line to film packet 16b, rather than bi-angularly, as in FIG. 6.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A locator for the nose cone of a dental x-ray machine for use with a radiographic film holder having a handle extending out of a patient's mouth, said locator comprising a socket shaped to receive a proximal end of said handle, an arm extending laterally of said socket and having a distal end, a ring attached to said distal end of said arm, said ring being shaped to receive and align the cone to direct x-rays emitted from said cone toward a film held in the holder.

2. A locator, according to claim 1, in which said ring is adjustable in position relative to said arm.

3. A locator according to claim 1, in which said distal end of said arm is formed with a pivot and said ring is formed with a sleeve fitting over said pivot, whereby, said ring is pivotally adjustable relative to said arm.

4. A locator according to claim 1, which further comprises a tab extending from said ring, said tab being formed with an aperture shaped to receive the handle.

5. A locator, according to claim 1 in which said arm has a first portion generally parallel to said socket, a curved portion beyond said first portion extending through approximately 90° of arc, and an outer portion beyond said curved portion extending approximately perpendicular to said socket.

6. A locator according to claim 1 in which said socket is formed with a rectangular cross-section opening to receive the handle.

7. A locator according to claim 6 in which said socket is formed with a detent to engage the handle to hold the handle in a position of adjustment relative to said locator.

8. In combination, a locator according to claim 1 and a retainer, said retainer comprising, a bite portion configured for placement between the patient's jaws, gripping means distal of said bite portion for gripping a film packet so that said film packet lies lingually of and adjacent selected teeth and said handle extending from said bite portion positioned to extended out from the patient's mouth, said handle being dimensioned to fit into said socket.

9. The combination of claim 8 in which said handle is slidable relative to said socket.

10. The combination of claim 9 in which said socket is formed with a detent to detachably secure said handle relative to said locator.

11. The combination of claim 8 in which said ring is adjustable in position relative to said arm to adjust the direction of x-rays emitted from said cone relative to a film packet held in said retainer.

12. The combination of claim 11 in which said retainer holds a film packet in at least three positions comprising a first film packet position behind teeth in the upper jaw, a second film packet position behind teeth in the bottom jaw and a third film packet position behind teeth in both upper and lower jaws, and said ring is adjustable in at least three ring positions to direct x-rays emitted from said cone toward a film packet held in any of said three film packet positions.

* * * * *